United States Patent [19]

Rivier et al.

[11] 4,218,439
[45] Aug. 19, 1980

[54] PEPTIDE WHICH INHIBITS GONADAL FUNCTION

[75] Inventors: Catherine L. Rivier; Jean E. F. Rivier; Wylie W. Vale, Jr., all of La Jolla, Calif.

[73] Assignee: The Salk Institute for Biological Studies, San Diego, Calif.

[21] Appl. No.: 917,781

[22] Filed: Jun. 26, 1978

Related U.S. Application Data

[63] Continuation-in-part of Ser. No. 815,590, Jul. 14, 1977, abandoned.

[51] Int. Cl.$^2$ ..................... A61K 37/00; C07C 103/52
[52] U.S. Cl. .......................... 424/177; 260/112.5 LH
[58] Field of Search ............... 424/177; 260/112.5 LH

[56] References Cited

U.S. PATENT DOCUMENTS

| | | | |
|---|---|---|---|
| 3,836,640 | 9/1974 | Laurence | 424/177 |
| 4,034,082 | 7/1977 | Johnson et al. | 260/112.5 LH |
| 4,081,533 | 3/1978 | Cheesman | 260/112.5 LH |

OTHER PUBLICATIONS

Sandow, et al., Acta Endocr. 84, Suppl. 208, p. 33 (1977).
Auclair, et al., BBRC 76 855–862 (1977).
Auclair, et al., Endocunology 101, 1890–1893 1977.
Pelletier, et al., Endocrinology 103, No. 2, pp. 641–643 1978.
Jaramillo, et al., Int. J. Fertil. 22 77 (1977).
Turner, et al., Fertility and Sterility 27, No. 5, p. 545 (1976).
Cory, et al., Biochem. and Biophys. Res. Comn. 67, 1975, pp. 576–582.

*Primary Examiner*—Delbert R. Phillips
*Attorney, Agent, or Firm*—Fitch, Even & Tabin

[57] ABSTRACT

A method for preventing reproduction by administering to male mammals a peptide which inhibits the secretion of gonadotropins by the pituitary gland and inhibits the release of steroids by the gonads. The peptide has the structure:

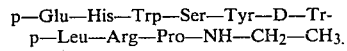

p—Glu—His—Trp—Ser—Tyr—D—Trp—Leu—Arg—Pro—NH—CH$_2$—CH$_3$.

5 Claims, No Drawings

PEPTIDE WHICH INHIBITS GONADAL FUNCTION

The invention described herein was made in the course of work under a grant or award from the Department of Health, Education, and Welfare.

The present application is a Continuation-In-Part of application Ser. No. 815,590, filed July 14, 1977 now abandoned.

The present invention relates to a peptide having influence on the release of gonadotropins by the pituitary gland in male mammalians, including humans. More particularly, the present invention is directed to a peptide which inhibits gonadal function and the release of male steroidal hormones.

The pituitary gland is attached by a stalk to the region in the base of the brain known as the hypothalamus. The pituitary gland has two lobes, the anterior and posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or glyco-protein molecules that travel through the blood stream to various organs and which, in turn, stimulate the secretion into the blood stream of other hormones from the peripheral organs. In particular, follicle stimulating hormone and luteinizing hormone are released by the pituitary gland. These hormones, in combination, regulate the functioning of the gonads to produce testosterone in the testes and progesterone and estrogen in the ovaries, as well as regulating the production and maturation of gametes. These hormones are sometimes referred to as gonadotropins or gonadotropic hormones.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly luteinizing hormone. For convenience, luteinizing hormone is hereinafter referred to as LH. The hypothalamic hormone which acts as a releasing factor for LH is referred to herein as LRF wherein RF stands for "releasing factor" and the L signifies that the hormone releases LH. LRF has been isolated and identified.

It has been demonstrated that some female mammalians who have no ovulatory cycle and who show no pituitary or ovarian defect begin to secrete normal amounts of the gonadotropins, LH and FSH (follicle stimulating hormone) after the administration of LRF. The administration of LRF is suitable for the treatment of those cases of infertility where the functional defect resides in the hypothalamus. Ovulation can be induced in female mammalians by the administration of LRF. However, the dosage level of LRF required to influence ovulation may sometimes be high. Recent reports have also indicated that the administration of large and frequent dosages of LRF actually inhibit gonadal function in female rats. For this reason, LRF has been investigated for its potential use as a contraceptive. The principal disadvantage to the use of LRF as a potential contraceptive is, of course, the requirement for large and frequent dosages.

It would be desirable to provide a peptide which inhibits secretion of steroids at much lower levels than LRF and which would require less frequent administration. It would also be desirable to provide a peptide which can be administered to male mammals to prevent reproduction. The pharmaceutical industry has made numerous efforts to develop a contraceptive which can be administered to male mammals.

The principal object of the present invention is to provide a peptide which inhibits the release of steroids by the gonads of male mammalians, including humans. Another object of the present invention is to provide a peptide which has an enhanced inhibitory effect on the reproductive processes of mammalians, including humans. A further object of the present invention is to provide a method for contraception by administering an effective amount of a particular peptide to male mammals.

These and other objects of the present invention will become more apparent from the following detailed description.

Generally, in accordance with the present invention, a peptide has been synthesized which directly or indirectly inhibits the secretion of gonadotropins by the pituitary gland of mammalians, including humans and inhibits the release of steroids by the gonads. The peptide acts to inhibit the release of gonadotropins at significantly lower levels of dosage when compared with known peptides which inhibit release of gonadotropins. The peptide can be used as a contraceptive for male mammals. The peptide can be administered by any suitable and convenient method, such as orally, by injection or subcutaneously. The peptide can be combined with suitable pharmaceutically acceptable carriers or diluents, such as vegetable oil, sugars, polysaccharides and gums.

LRF has been characterized as a decapeptide having the following structure:

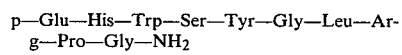

Peptides are compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino groups is identified by numbering the amino groups from left to right. In the case of LRF, the hydroxyl portion of the carboxyl group has been replaced with an amino group ($NH_2$). The abbreviations for the individual amino acid groups above are conventional and are based on the trivial name of the amino acid: where pGlu is pyroglutamic acid, His is histidine, Trp is tryptophan, Ser is serine, Tyr is tyrosine, Gly is glycine, Leu is leucine, Arg is arginine and Pro is proline. Except for glycine, amino acids are of the L-configuration unless noted otherwise.

It is known that the substitution of D-Ala or D-Lys for Gly in the 6-position of the LRF decapeptide provides a peptide material having from 3 to 10 times greater potency than does LRF to effect the release of luteinizing hormone and other gonadotropins by the pituitary gland of mammalians. The releasing effect is obtained when the substituted peptide is introduced into the blood stream of a mammalian.

It is also known that substitution of various amino acids for His (or the deletion of His) at the 2-position of the LRF decapeptide produces peptide materials having an inhibitory effect on the release of luteinizing hormone and other gonadotropins by the pituitary gland of mammalians. In particular, varying degrees of inhibition of the release of luteinizing hormone are obtained when His is deleted or replaced by Asp, Cys, D-Ala, des His, D-Phe and Gly. It has been further discovered that the inhibitory effect of those peptides modified at the 2-position can be greatly enhanced when D-Ala or D-Lys is substituted for Gly in the 6-position of the decapeptides. For example, the peptide: p—Glu—Trp—Ser—Tyr—D—Ala—Leu—Arg—Pro—Gly—$NH_2$ is 3 times more potent as an inhibitor for the release of gonadotropins than is the same peptide where Gly is present in the 6-position rather than D-Ala.

In accordance with the present invention, a peptide has been synthesized which is about 150 times more potent than LRF. This peptide has been found to be effective to prevent reproduction when administered periodically to male mammals at very low levels of dosage.

The peptide used in the method of the present invention is represented by the following formula:

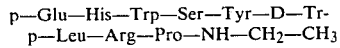

p—Glu—His—Trp—Ser—Tyr—D—Trp—Leu—Arg—Pro—NH—$CH_2$—$CH_3$

The peptide of the present invention was synthesized by a solid phase technique. The synthesis was conducted in a stepwise manner on chloromethylated resin. The resin was composed of fine beads (20–70 microns in diameter) of a synthetic resin prepared by copolymerization of styrene with 1 to 2 percent divinylbenzene. The benzene rings in the resin were chloromethylated in a Friedel-Crafts reaction with chloromethyl ether and stannic chloride. The chlorine thus introduced is a reactive benzyl chloride type of linkage. The Friedel-Crafts reaction is continued until the resin contains 0.5 to 2 millimoles of chlorine per gram of resin.

As described hereinbelow, the reagents used will be first listed by their chemical name and their common abbreviation. Thereafter, the reagent will sometimes be referred to by the common abbreviation.

The triethylammonium salt of N α Boc protected Pro is esterfied onto the chloromethylated resin by refluxing in ethanol for about 48 hours. Also possible is the use of the resin or potassium salts in dimethylformamide (DMF) or dimethylsulfoxide (DMS) respectively of temperatures ranging from 40° to 80° C. After deprotection and neutralization, the N α Boc derivative of the next amino acid, Arg is added along with a coupling agent which is dicyclohexylcarbodiimide (DCC). The side chain of Arg is protected with tosyl (Tos). Deprotection, neutralization and addition of successive amino acids is performed in accordance with the following schedule:

Schedule for coupling of amino acids in solid phase synthesis of p—Glu—His—Trp—Ser—D—Trp—Leu—Arg—Pro—NH—$CH_2$—$CH_3$ on 10 grams of resin.

| Step | Reagents and Operations | Mix Times Min. |
|---|---|---|
| 1 | $CH_2Cl_2$ wash 80 ml (2 times) | 3 |
| 2 | Methanol (MeOH) wash 30 ml (2 times) | 3 |
| 3 | $CH_2Cl_2$ wash 80 ml (3 times) | 3 |
| 4 | 50 percent trifluoroacetic acid (TFA) plus 5 percent 1,2-ethanedithiol in $CH_2Cl_2$ 70 ml (2 times) | 10 |
| 5 | $CH_2Cl_2$ wash 80 ml (2 times) | 3 |
| 6 | Triethylamine ($Et_3N$) 12.5 percent in dimethylformamide (DMF) 70 ml (2 times) | 5 |
| 7 | MeOH wash 40 ml (2 times) | 2 |
| 8 | $CH_2Cl_2$ wash 80 ml (3 times) | 3 |
| 9 | Boc-amino acid (10 mmoles) in 30 ml DMF (1 time) plus dicyclohexylcarbodiimide (DCC) (10 mmoles) in DMF | 30 |
| 10 | MeOH wash 40 ml (2 times) | 3 |
| 11 | $Et_3N$ 12.5 percent in DMF 70 ml (1 time) | 3 |
| 12 | MeOH wash 30 ml (2 times) | 3 |
| 13 | $CH_2Cl_2$ wash 80 ml (2 times) | 3 |

After step 13, an aliquot is taken for a ninhydrin test: if the test is negative, go back to step 1 for coupling of the next amino acid; if the test is positive or slightly positive, go back to steps 9 through 13.

The above schedule is used for coupling of each of the amino acids of the peptide of the invention. N α Boc protection is used for each of the remaining amino acids throughout the synthesis. OBzl is used as a side chain protecting group for Ser and Tyr. 2–6 dichlorobenzyl can be used as the side chain protecting group for Tyr. Tos, dinitrophenyl (Dnp) or Boc can be used as the side chain protecting group for His. P-Glu is introduced as benzyloxycarbonyl (Z) protected amino acid.

Cleavage of the peptide from the resin is performed by stirring the resin overnight in distilled ethylamine at 0° C. in a pressure bottle. After removal of excess ethylamine by distillation under nitrogen or vacuum, the resin, suspended in methanol, is removed from the slurry by filtration. The resin is further washed successively with DMF, methanol, DMF and methanol. The recovered solution of cleaved, protected peptide is evaporated to dryness on a rotary vacuum evaporator at room temperature. The peptide is taken in a minimum amount of methanol to dissolve the peptide. The solution is added dropwise to a 50 times volume excess of dry ether with stirring. A flocculent precipitate appears which is recovered by filtration or centrifugation. The recovered precipitate is dried and deprotected.

Deprotection of the peptide takes place at 0° C. with hydrofluoric acid (HF). Anisole is added to the peptide prior to treatment with HF. After the removal of HF, under vacuum, the peptide is treated with ether, decanted, taken in dilute acetic acid and lyophilized.

Purification of the peptide is effected by ion exchange chromotography on a CMC column, followed by partition chromotography using the elution system: n-butanol; acetic acid; water (4:1:5; volume ratio). The partition chromotography column packing is Sephadex G 25.

The peptide is used at a level effective to prevent reproduction by male mammals. It has been determined that the peptide of the invention is effective at levels as low as 0.5 microgram per kilogram of body weight per day for 7 days to reduce testes and seminal vesicle weights. Testosterone levels were comparable to those of control animals within one week following cessation of treatment for 7 days. Prostate weights recover in 2 weeks and seminal vesicle weights in 4 weeks. It is preferred to use dosage levels in the range of from about 0.5 to about 50 micrograms per kilogram of body weight per day. Higher levels can be used but no significant benefit is attained through use of higher levels.

The following example further illustrates various features of the invention, but is intended to in no way limit the scope of the invention which is defined in the appended claims.

EXAMPLE I

It has been determined that the treatment of male rats with 10 micrograms of the peptide once a day for 7 days results in a decrease in testis and seminal vesicle weight, spermatogenesis and plasma androgen levels. However, immunoreactive gonadotropin levels in the treated male animals were elevated relative to control animals. See Table I.

TABLE I

|  |  | Male Rats | | | | |
|  |  | Wt. Grams | | Ng/Ml Plasma | | |
|  |  | Testis | Sem. V. | LH | FSH | Test. | DHT |
| --- | --- | --- | --- | --- | --- | --- | --- |
| Treatment | N | | | | | | |
| Control | 8 | 2.09 | 0.41 | 58 | 718 | 4724 | 756 |
| 10 μG peptide for 15 days | 8 | 1.33 | 0.18 | 561 | 1582 | 229 | 151 |

Histological examination of the testes following the 7-day treatment revealed tubular damage, arrested spermatogenesis and degenerated Sertoli cells for a period up to several weeks following cessation of the daily injections. The rats were capable of effecting coitus following cessation of the injections but were incapable of causing fertilization.

It is thus evident that the peptide of the present invention is useful as a contraceptive for males.

We claim:

1. A method for inhibiting the release of steroids by the gonads of male mammals comprising administering to a male mammal an effective amount of a peptide having the formula

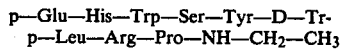

2. A method in accordance with claim 1 wherein said peptide is administered at a level of from about 0.5 to about 50 micrograms per kilogram of body weight per day.

3. A method for preventing conception by female mammals comprising administering an effective amount of a peptide to a male mammal, said peptide having the formula

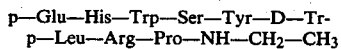

4. A method in accordance with claim 3 wherein said peptide is administered at a level of from about 0.5 to about 50 micrograms per kilogram of body weight per day.

5. A method in accordance with claim 1 wherein a sufficient amount of said peptide is administered periodically so that spermatogenesis is so reduced that said male mammal is incapable of fertilization of an ovum in a mating female.